United States Patent
Satterfield

[11] Patent Number: 6,146,398
[45] Date of Patent: Nov. 14, 2000

[54] ANTISEPTIC TOOL FOR BODY PIERCED OPENINGS

[76] Inventor: Richard A. Satterfield, 5158 Cove Rd., Jasper, Ga. 30143

[21] Appl. No.: 09/393,425

[22] Filed: Sep. 10, 1999

[51] Int. Cl.$^7$ ........................................................ A61F 9/00
[52] U.S. Cl. .......................................................... 606/162
[58] Field of Search .................... 606/162, 188, 606/222; 604/1, 2, 15, 358, 11, 286; 132/321; 131/245

[56] References Cited

U.S. PATENT DOCUMENTS

| | | | |
|---|---|---|---|
| 4,497,402 | 2/1985 | Karos | 606/162 |
| 4,798,216 | 1/1989 | McCarty et al. | 606/162 |

*Primary Examiner*—Michael Buiz
*Assistant Examiner*—(Jackie)Tan-Uyen T Ho
*Attorney, Agent, or Firm*—William B. Noll

[57] ABSTRACT

A hand manipulated tool to cleanse and apply medication to a pierced body hole, such as an earlobe. The tool comprises an elongated member sized to slidably engage the pierced body hole. The tool is further characterized by first and second sections, where the first section is a cleansing section, and the second section has a medication absorbent layer to effect treatment of the pierced body hole.

4 Claims, 1 Drawing Sheet

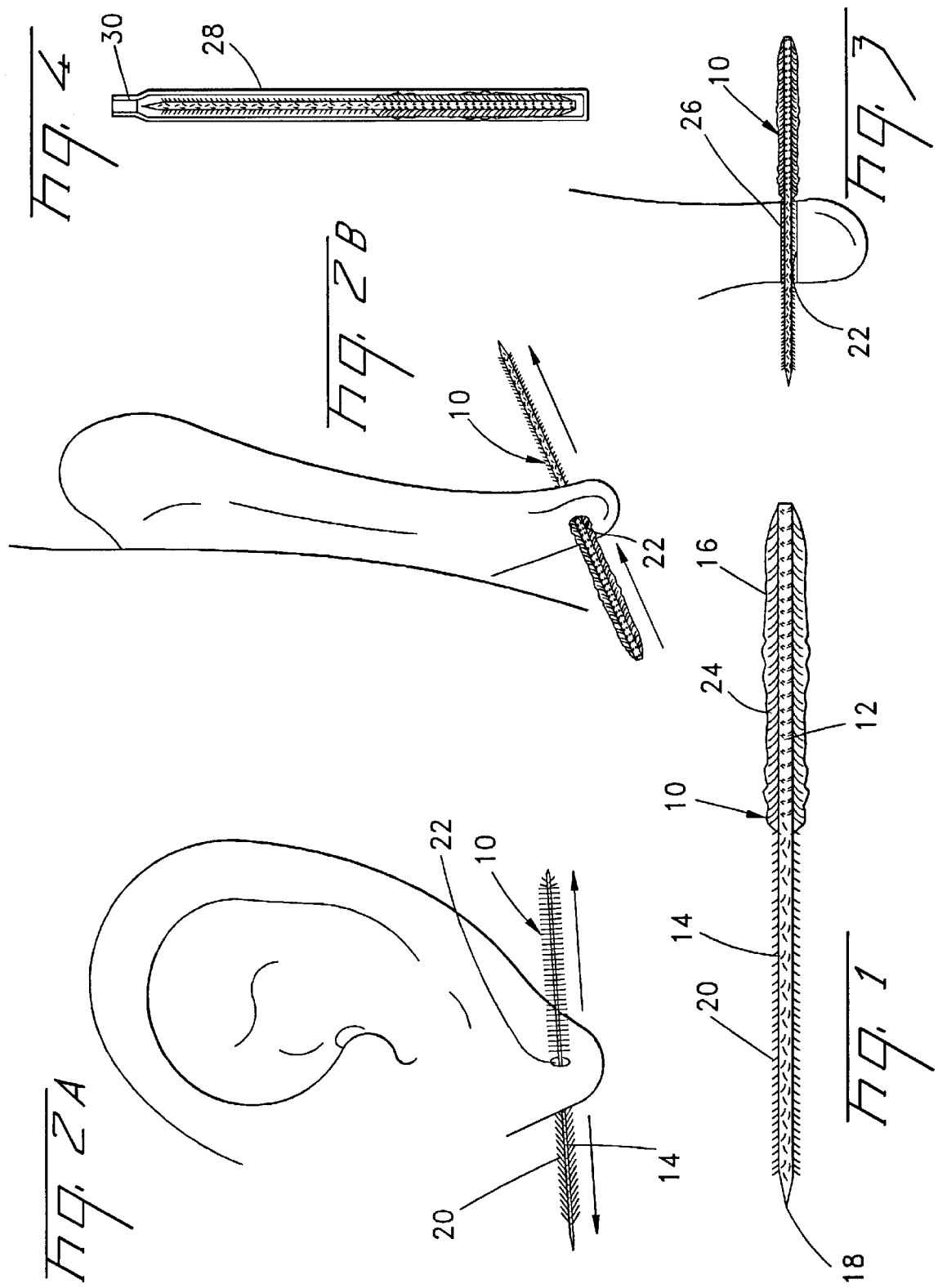

ANTISEPTIC TOOL FOR BODY PIERCED OPENINGS

FIELD OF THE INVENTION

This invention is directed to the field of hand held tools or devices for cleansing and applying an antiseptic medication to a pierced hole, such as for a person's pierced earlobe.

BACKGROUND OF THE INVENTION

The present invention is directed to a hand held tool for cleaning and applying an antiseptic to a pierced body part, and may be particularly valuable to a freshly pierced body part where infection may result in a painful situation. Though earlobes may be the most common body part to be pierced, current lifestyles reveal that various and different body parts are being pierced to receive an earring or other ornamentation. Accordingly, the invention should not be limited to ear piercing, but rather body piercing, and the treatment thereof, in general.

It is now a common practice to pierce body parts, such as one's earlobes, so that earrings can be worn. This practice spans all ages, from infants to adults, male and female. Currently, it is popular to place multiple holes in an earlobe, and even continuing up to the top of the ear, so that many earrings may be worn at the same time.

The holes in the earlobes may be subject to infection at the initial piercing, or over time may be subject to buildup of residue including dried soap and shampoo, body oils and skin shed by the scar tissue formed around the hole. These residues can collect in the hole and on the earrings facilitating the growth of bacteria which can lead to further infection. As a result frequent cleansing and treatment is critical to a wearer of body piercing ornamentation.

The prior art describes a number of devices or systems for cleaning or applying medication to a pierced body part, most commonly an earlobe. Such devices or systems are reflected in the following U.S. patents:

a.) U.S. Pat. No. 5,183,461, to Hobbs, relates to a strand device for pierced earlobe cleansing, and comprises a flexible monofilament nylon or nylon-like material which is folded in half so that the two ends meet and are parallel. The ends are bonded by heating and melting the strands to form a single stem from the two strands, the stem having a greater stiffness than the single strand alone. The melting simultaneously creates a rounded tip at the end of the stem. The ends of the strand are joined so that a loop remains open at the fold. The stem is sufficiently stiff so that it can be fed through a pierced ear hole with the rounded end of the stem facilitating feeding the stem through the hole. The loop, which normally is open is compressed as the stem is pulled out the opposite side of the ear. The resilience of the loop is sufficient to permit it to remain slightly expanded so that its greater diameter "scrapes" the ear hole as it passes through. The loop resiles to its original shape as it exits the ear hole.

b.) U.S. Pat. No. 4,798,216, to McCarty et al., also discloses a threaded member for cleansing a pierced earlobe. The thread is impregnated with a hypo-allergenic, anti-bacterial astringent for cleansing and conditioning pierced ear lobes.

c.) U.S. Pat. No. 4,497,402, to Karos, teaches an apparatus for cleaning and sterilizing ear lobe holes for pierced earrings which utilizes a string of absorbent material having attached thereto a firm tip. Both the string and the tip are maintained in a sealed envelope adjacent a pad of absorbent material saturated with an antiseptic fluid in contact with the string to saturate the string with the fluid. When it is desired to clean and sterilize the ear lobe hole, the package and the string and tip are run through the ear lobe hole. The string both cleans the ear lobe hole and imparts the sterilizing fluid to the hole.

d.) U.S. Pat. No. 4,353,370, to Evans, is directed to a device for cleaning the pierced ear hole of the earlobe. A grooved or ruffled rod member containing an absorbent material loaded with a cleaning agent is adapted to be passed into and out of the earlobe hole and then disposed of. In another embodiment, the ear rod is constructed as part of a permanent earring which can be worn to provide a constant supply of cleaning solution to the earlobe to prevent infection of the ear hole.

e.) U.S. Pat. No. 4,041,946, to Barton, relates to a medicated member that is adapted to be passed through the ear lobe of a pierced ear and to be retained therein thereby speeding the healing of the process.

f.) U.S. Pat. No. 3,500,829, to Abramowitz, teaches an apparatus for piercing the lobe of a human ear with a minimum of pain and with means for substantially eliminating the possibility of infection thereafter and while wearing the earring.

g.) U.S. Pat. No. Des. 346,443, to Franklin, is directed to a pierced ear cleaner device.

While the prior art offers some assistance to provide cleansing and applying medication to pierced earlobes, none appear to give the simplicity and effectiveness of the present invention. The manner by which this simplicity and effectiveness is achieved will become more apparent from the following description, particularly when read in conjunction with the accompanying drawings.

SUMMARY OF THE INVENTION

The present invention relates to a cleansing and medicating hand tool for treating body piercing holes, such as pierced earlobes. The tool comprises an elongated core of predetermined length, with a diameter sized to be slidably inserted into the body piercing hole, such as a polyester filament, having first and second sections extending from a midpoint thereof to the respective free ends of the core. A first section preferably includes plural, thin and flexible barb like elements angularly disposed to the core, and the second section includes an absorbing layer of material capable of receiving and applying an anti-bacterial astringent.

Accordingly, an object of this invention is the provision of a simple, yet effective means for both cleaning and medicating a body piercing hole to eliminate the potential for infection.

Another object hereof is to provide a sealed tube containing the hand tool hereof along with a quantity of anti-bacterial astringent.

These and other objects will become more apparent to those skilled in the art from a reading of the following description.

BRIEF DESCRIPTION OF DRAWINGS

FIG. 1 is a plan view of the hand held tool according to the present invention.

FIGS. 2A and 2B are perspective views of a pierced earlobe of the user of the tool hereof, showing, the cleansing, and medicating of such pierced earlobe.

FIG. 3 is partial sectional view of the ear and tool of FIG. 2A.

FIG. 4 is a plan view illustrating an exemplary packaging tube containing the hand held tool of FIG. 1, said tube further containing a medication fluid.

DETAILED DESCRIPTION OF PREFERRED EMBODIMENT

This invention relates to a hand held tool or applicator for cleaning and applying an antiseptic, such as an anti-bacterial stringent, to a person's pierced body part, such as a pierced earlobe. The tool is illustrated in the several Figures, where like reference numerals represent like components or features throughout the various views.

Turning now to the several Figures, the hand held tool 10, as best seen in FIG. 1, comprises a central core 12, typically several inches in length and of a small diameter so as to be slidably received within the pierced opening, such as a polyester filament, having a first section 14 and a second section 16. The first section 14 is characterized by a pointed distal end 18, and features a plurality of thin flexible barbs 20 angularly disposed to the axis of the core. As best seen in FIG. 2A, the tool 10 is inserted into the pierced opening 22 to effect an initial cleaning thereof by the flexible barbs 20, or fiberous arms.

The second section 16 is provided with a layer 24 of absorbent type material, such as cotton. A suitable medication or cleansing solution, or an anti-bacterial stringent, may be absorbed into the layer 24, whereby such medication, etc. will be transferred by contact with the exposed surfaces 26 (FIG. 3) of the pierced opening 22.

This simple, yet effective tool 10 allows cleaning of the pierced opening to remove debris or dried skin therefrom with a repeated or back and forth movement of the first section 14 (FIG. 2A), followed by further movement of the tool to pass the medication carrying second section 16 through the pierced opening 22.

Further, as illustrated in FIG. 4, the tool hereof may be conveniently packaged in a disposable tube 28, sealed at one end 30 for convenient handling. The slender disposable tube 28 also contains the anti-bacterial stringent, for example. By simply removing or breaking the sealed end 30, the user thereof is provided with a clean and fresh means to treat the pierced body opening.

It is recognized that modifications and variations may be made to the hand held tool of this invention. Accordingly, no undue limitations should be imposed thereon except as set forth in the following claims.

What is claimed is:

1. A hand held tool for cleansing and medicating a body pierced hole, where such hole may be subject to infection and debris buildup, said tool comprising:

a thin, semi-rigid, elongated core having first, and second segments joined together at an intermediate position along said core, said first segment containing a plurality of flexible, fibrous arms extending therefrom to provide cleansing to said body pierced hole, and said second segment containing a thin, encircling layer of absorbent material thereabout for applying medication to said cleansed body pierced hole.

2. The hand held tool according to claim 1, wherein said core is made of a polyester filament, and said flexible, fiberous arms extend angularly to said core, and are integrally formed with said core.

3. The hand held tool according to claim 1, wherein said encircling layer of absorbent material is cotton.

4. The hand held tool according to claim 1, wherein said first segment includes a tapered distal end.

* * * * *